United States Patent [19]

Kleiner

[11] 4,427,602
[45] Jan. 24, 1984

[54] PROCESS FOR THE PREPARATION OF VINYLPHOSPHONIC ACID DICHLORIDE AND 2-CHLOROETHANEPHOSPHONIC ACID DICHLORIDE

[75] Inventor: Hans-Jerg Kleiner, Kronberg, Fed. Rep. of Germany

[73] Assignee: Hoechst Aktiengesellschaft, Frankfurt am Main, Fed. Rep. of Germany

[21] Appl. No.: 359,235

[22] Filed: Mar. 18, 1982

[30] Foreign Application Priority Data

Mar. 20, 1981 [DE] Fed. Rep. of Germany ....... 3110976

[51] Int. Cl.³ .............................................. C07F 9/42
[52] U.S. Cl. ................................................ 260/543 P
[58] Field of Search ..................................... 260/543 P

[56] References Cited

U.S. PATENT DOCUMENTS 4,013,715 3/1977 Finke et al. .................... 260/543 P Primary Examiner—Natalie Trousof
Assistant Examiner—L. Hendriksen
Attorney, Agent, or Firm—Curtis, Morris & Safford

[57] ABSTRACT

Process for the preparation of vinylphosphonic acid dichloride and 2-chloroethanephosphonic acid dichloride, by heating a 2-acetoxyethanephosphonic acid dialkyl ester of the general formula

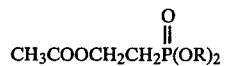

wherein R denotes alkyl groups having 1 to 4 carbon atoms, in the presence of acid or basic catalysts at 150°–270° C. with elimination of an alkyl acetate, reacting the resulting reaction mixture with water at temperatures between 130°–230° C. while simultaneously distilling off the alcohol formed, and reacting the crude vinylphosphonic acid thus formed with phosgene in the presence of catalysts and also in the presence of phosphonic acid dichlorides.

4 Claims, No Drawings

PROCESS FOR THE PREPARATION OF VINYLPHOSPHONIC ACID DICHLORIDE AND 2-CHLOROETHANEPHOSPHONIC ACID DICHLORIDE

2-Chloroethanephosphonic acid derivatives containing 2-chloroethyl ester groups are starting materials for the preparation of 2-chloroethanephosphonic acid dichloride, from which vinylphosphonic acid dichloride can be prepared by elimination of hydrogen chloride (German Patent Specification No. 2,132,962; German Patent Specification No. 2,357,678). Considerable amounts of 1,2-dichloroethane are obtained in this process during the preparation of 2-chloroethanephosphonic acid dichloride. In addition to a disadvantageous influence on the space-time yield by the 1,2-dichloroethane this by-product is undesirable because it constitutes a danger to health at the place of work. Processes are therefore sought in which 1,2-dichloroethane is no longer produced.

It has now been found that vinylphosphonic acid dichloride and 2-chloroethanephosphonic acid dichloride can be prepared in a simple and economic manner by heating a 2-acetoxyethanephosphonic acid dialkyl ester of the general formula $$CH_3COOCH_2CHP(OR)_2$$
$$\overset{O}{\|}$$

wherein R denotes alkyl groups having 1 to 4, preferably 1 to 2, carbon atoms, in the presence of acid or basic catalysts at 150°–270° C., preferably 170°–230° C., an alkyl acetate of the general formula $$CH_3COOR$$

wherein R has the abovementioned meaning, being eliminated, reacting the resulting reaction mixture with water at temperatures between 130°–230° C., preferably 140°–175° C., while simultaneously distilling off the alcohol formed of the general formula $$ROH$$

wherein R has the abovementioned meaning, and reacting the crude vinylphosphonic acid thus formed with phosgene in the presence of basic catalysts, but also alkali metal salts, and also in the presence of phosphonic acid dichlorides. Phosphonic acid dichlorides obtained in this process are very pure and free from by-products. They are obtained in high yields.

It is surprising that acid chlorides obtained in this multi-stage process are obtained in a high yield and virtually free from by-products.

Examples of possible starting materials are the dimethyl, diethyl, diisopropyl and di-n-butyl ester of 2-acetoxyethanephosphonic acid. The 2-acetoxyethanephosphonic acid dimethyl ester is particularly preferred.

Numerous compounds are possible as acid or basic catalysts. Acid catalysts used can be:

(A) sulfuric acid or phosphoric acid (B) a halogen-containing carboxylic acid having a $P_{Ka}$ value <2.5, such as dichloroacetic acid, trichloroacetic acid or trifluoroacetic acid (C) aromatic sulfonic acids having a $P_{Ka}$ value <2.5, such as benzenesulfonic acid or p-toluenesulfonic acid (D) preferably phosphinic acids having 2 to 18 carbon atoms, such as dimethylphosphinic acid, methylethylphosphinic acid, dioctylphosphinic acid, methylphenylphosphinic acid or diphenylphosphinic acid (E) particularly preferably phosphonic acids having 1 to 18 carbon atoms and their half-esters having 1 to 4 carbon atoms in the alcohol radical, such as methanephosphonic acid, propanephosphonic acid, propanephosphonic acid monomethyl ester, octadecanephosphonic acid, 2-acetoxyethanephosphonic acid, 2-acetoxyethanephosphonic acid monomethyl ester, vinylphosphonic acid, vinylphosphonic acid monomethyl ester, vinylphosphonic acid monoethyl ester or benzenephosphonic acid (F) likewise particularly preferably pyrophosphonic acids or their half-esters, such as methanepyrophosphonic acid, benzenepyrophosphonic acid, vinylpyrophosphonic acid or vinylpyrophosphonic acid monomethyl ester (G) acid reaction mixtures which are produced in the process according to the invention are also highly suitable.

Basic catalysts used can be:

(A) Tertiary aliphatic and aromatic amines and phosphines having 3 to 18 carbon atoms, such as trimethylamine, tripropylamine, tributylamine, triphenylamine, trimethylphosphine, triethylphosphine, tripropylphosphine, tributylphosphine, triphenylphosphine and tris-(p-dimethylaminophenyl)-phosphine and the corresponding mixed amines, phosphines, phospholanes and phospholenes, such as dimethylethylamine, diethylbutylamine, N-dimethylaniline, 4-methyl-N-dimethylaniline, N-diethylaniline, N,N-tetramethylphenyldiamine or N-methylpyrrolidine; methyldiethylphosphine, dimethylpropylphosphine, diethylbenzylphosphine, 1-methylphosphol-3-ene and 1-ethyl-3-methylphosphol-3-ene.

(B) Quaternary ammonium salts and phosphonium salts having 3 to 18 carbon atoms, such as tetramethylammonium chloride, tetramethylammonium bromide or tetraethylphosphonium chloride, trimethylbenzylammonium chloride, triethylbenzylammonium chloride, triethylbenzylammonium bromide, trimethylbenzylphosphonium chloride or triphenylethylphosphonium-2,4-diaminobenzosulfonate.

(C) Heterocyclic compounds having aromatic character, such as pyridine, quinoline, their various alkyl and dialkyl, preferably methyl or dimethyl derivatives, imidazole, N-vinylimidazole, benzothiazole, 2-amino-6-ethoxybenzothiazole, and also phosphabenzoles.

(D) Acid amides, such as dimethylformamide, N-dimethylacetamide, N-diethylpropionamide, N-dimethylbenzamide, N-methylpyrrolidone or N,N'-tetramethylterephthalic acid diamide or ureas, such as tetramethylurea or trimethylphenylurea.

(E) Other nitrogen compounds or phosphorus compounds having a higher valency of one N atom or P atom than 3, such as pyridine-N-oxide, trimethylphosphine oxide, tributylphosphine oxide, trihexylphosphine oxide, triphenylphosphine oxide, dimethylphenylphosphine oxide, dimethylphenylphosphine sulfide, dimethylchloromethylphosphine oxide, dimethyleicosylphosphine oxide, dimethyldodecylphosphine oxide, dimethylphosphine oxide, dimethylpyrrolidinyl-1-methylphosphine oxide, triphenylphosphine dichloride, dimethyldodecylphoshine sulfide, triphenylphosphineimine, dimethylchloromethylphosphine dichloride, N-2-dimethylphosphinylethylmethylacetamide or N-2-dimethylphosphinylethylmethylamine, or phospholene oxide, such as 1-methylphosphol-1-ene oxide or 1-ethyl-3-methylphosphol-1-ene oxide.

(F) Amides of phospinous and phosphonous acid and of phosphinic and phosphonic acids and also their thio analogs, such as ethanephosphonic acid bis-diethylamide, methanebutanephosphinous acid dimethylamide or diethylphosphinous acid isobutylamide. Also triamides of phosphoric and of thiophosphoric acid, such as hexamethylphosphoric acid triamide.

(G) Alkali metal carbonates, preferably sodium carbonate or potassium carbonate, alkali metal hydroxides, preferably sodium hydroxide or potassium hydroxide, alkali metal alcoholates, preferably sodium methylate.

In particular the sodium salts or potassium salts of the acids mentioned under A to F which have been mentioned as acid catalysts can be used as alkali metal salts.

The catalysts are used in amounts of 0.01 to 10, preferably 0.1 to 5, % by weight. When vinylphosphonic acid, monoalkyl esters thereof or acid reaction mixtures already obtained are used, even larger amounts of 10 to 50% by weight can be used.

The process is in general carried out by mixing the starting material with the catalyst and raising the mixture to the required reaction temperature of 150° to 270° C., preferably 170° to 230° C.

Higher temperatures are possible, but they do not yield any benefit. The danger of an increased formation of by-products, but also of polymerization, then arises.

The alkyl acetate being eliminated is then distilled off together with small amounts of an alkanol and of a dialkyl ether. The distillation is carried out under atmospheric pressure, if appropriate with the aid of an inert gas, such as, for example, nitrogen. However, in particular cases it may be advantageous to distil off in vacuo. The elimination of the alkyl acetate is complete after 2 to about 20 hours. It can be advantageous to continue stirring thereafter for another 1 to 4 hours at the reaction temperature, but also at higher temperatures. The process can also be carried out continuously.

It can be advantageous to add polymerization inhibitors, such as, for example, hydroquinone, hydroquinone monomethyl ether or phenothiazine.

If 2-acetoxyethanephosphonic acid diesters which are contaminated from their preparation with small amounts of the corresponding monoester are used as a starting material, a further addition of a catalyst is not necessarily required. It is here advantageous to start the reaction at about 250° C. When the acid reaction product which actually also acts as a catalyst for the elimination has been formed to a sufficient extent, the process can be continued at lower temperatures, for example at 180° to 220° C.

The reaction mixture produced in this elimination reaction essentially contains vinylphosphonic acid derivatives, vinylpyrophosphonic acid derivatives, oligomeric pyrophosphonic acid derivatives and derivatives of 2-hydroxyethanephosphonic acid together with phosphoric acid derivatives. The reaction mixture is then reacted in the form in which it is obtained at the required reaction temperature with water, the resulting alcohol being advantageously distilled off via a column. This reaction can produce small amounts of a dialkyl ether and of olefins. The reaction with water is complete when no more alcohol is eliminated. It can be advantageous in this reaction to employ larger amounts of water towards the end of the reaction and to distil off a part of the unreacted water together with the alcohol. The pressure to be selected according to the process is not critical, but the process is preferably carried out under approximately atmospheric pressure.

The reaction temperatures in this process step are between 130°–230° C. The reaction can also be carried out above 230° C., but a decomposition of vinylphosphonic acid is then expected to take place to an increasing extent. The reaction is preferably carried out within the temperature range 140°–175° C.

The reaction with water can also be carried out continuously.

The reaction with water produces crude vinylphosphonic acid which contains, in addition to 2-hydroxyethanephosphonic acid and derivatives of 2-hydroxyethanephosphonic acid, in particular also phosphoric acid. The resulting crude vinylphosphonic acid is finally phosgenated in a further reaction step, namely at temperatures of 90° to 200° C., preferably 120°–170° C., in the presence of basic catalysts or alkali metal salts of acids listed under A to F above and also in the presence of phosphonic acid dichlorides. If the elimination of alkyl acetates was already carried out in the presence of these catalysts, a further addition of catalysts is now not necessary.

The process can be carried out continuously just like the first reaction stage. It can also be advantageous to add polymerization inhibitors already mentioned above. Suitable catalysts which must necessarily be present in this phosgenation are basic catalysts as listed above for the first stage and also alkali metal salts of the acids mentioned above under A to F.

The phosgenation can be carried out in principle by adding from the start phosphonic acid dichlorides. Suitable for this purpose are $C_1$–$C_{12}$-alkanephosphonic acid dichlorides, for example methane-, ethane- or propanephosphonic acid dichloride, but preferably vinylphosphonic acid dichloride, particularly preferably 2-chloroethanephosphonic acid dichloride or mixtures of these acid chlorides. The total amount of these phosphonic acid dichlorides is about 5 to 200, preferably 20 to 100, % by weight, relative to the vinylphosphonic acid derivatives (1st stage).

This phosgenation produces a mixture of vinylphosphonic acid dichloride and 2-chloroethanephosphonic acid dichloride. The preparation of vinylphosphonic acid dichloride can be optimized by adding right at the start of the phosgenation a certain amount of 2-chloroethanephosphonic acid dichloride. Practical experience has shown that the best yield of vinylphosphonic acid dichloride is obtained if a mixture of vinylphosphonic acid dichloride and 2-chloroethanephosphonic acid dichloride is initially introduced. If desired, preliminary experiments can readily determine the amount of phosphonic acid dichloride which must be present in the chlorination to achieve a maximum yield of vinylphosphonic acid dichloride and/or chloroethanephosphonic acid dichloride. At the end of the phosgenation the same quantity of 2-chloroethanephosphonic acid dichloride which was added at the start of the reaction is then obtained, whilst on the other hand considerably more vinylphosphonic acid dichloride is produced than originally added. It is of course also possible to direct the reaction by the initial introduction of suitable amounts of vinylphosphonic acid dichloride in such a manner that 2-chloroethanephosphonic acid dichloride is obtained essentially or exclusively. The type and amount of phosphonic acid dichloride required for achieving a certain result depends in a particular case on the reaction conditions, such as time, temperature and type of catalyst.

After the chlorination is complete, a mixture of vinylphosphonic acid dichloride and 2-chloroethanephosphonic acid dichloride is obtained which can be separated readily by distillation. The two compounds are important organic phosphorus intermediate products in the preparation of compounds for a flame-retardant finish and for the preparation of 2-chloroethanephosphonic acid which is used as a growth regulator in plant protection.

EXAMPLE 1

A mixture of 50 g of vinylphosphonic acid and 100 g of 2-acetoxyethanephosphonic acid dimethyl ester was heated to about 180° C. while stirring, and 450 g of 2-acetoxyethanephosphonic acid dimethyl ester were then added dropwise in the course of 10 hours, during which period the temperature was increased to 192° C. 205 g of methyl acetate were distilled off simultaneously. 7 g of dimethyl ether were collected in a downstream cold trap. The resulting residue of 374 g was further heated for one hour at 200° C. The residue was then reacted at 160°–170° C. for 6 hours with water and the resulting methanol was distilled off simultaneously via a 1 m column with a silver-coated jacket. 366 g of crude vinylphosphonic acid were obtained. 164 g of this crude vinylphosphonic acid were added dropwise at 140°–150° C. in the course of 20 hours while stirring vigorously to a mixture of 136.7 g of 2-chloroethanephosphonic acid dichloride, 27.3 g of vinylphosphonic acid dichloride and 1 g of phosphoric acid tris-dimethylamide, during which period phosgene was passed into the reaction mixture. Excess phosgene present in the reaction batch was then flushed out by means of nitrogen at room temperature and the residue was distilled at 2 mm Hg. 186 g of vinylphosphonic acid dichloride, 157.5 g of 2-chloroethanephosphonic acid dichloride and 19 g of a distillation residue were obtained. The yield of vinylphosphonic acid dichloride was 72.5% of theory and of 2-chloroethanephosphonic acid dichloride 7.5% of theory, relative to crude vinylphosphonic acid employed.

EXAMPLE 2

A mixture of 50 g of vinylphosphonic acid and 100 g of 2-acetoxyethanephosphonic acid dimethyl ester was heated while stirring to 180° C., and 450 g of 2-acetoxyethanephosphonic acid dimethyl ester were then added dropwise in the course of 10 hours, during which period the temperature was increased to 190° C. 205 g of methyl acetate were distilled off simultaneously. 7 g of dimethyl ether were collected in a downstream cold trap. The resulting residue of 374 g was reacted for 6 hours with water at 160°–175° C., during which period the resulting methanol was distilled off via a column. 374 g of crude vinylphosphonic acid, still containing water, were obtained. 174 g of this crude vinylphosphonic acid were added dropwise at 140° C. in the course of 12 hours while stirring vigorously to a mixture of 145 g of vinylphosphonic acid dichloride and 1 g of tris-methylphosphine oxide, during which period phosgene was passed into the reaction mixture. Excess phosgene present in the reaction batch was then flushed out by means of nitrogen at room temperature and the residue was distilled under 2 mm Hg. 185.5 g of vinylphosphonic acid dichloride, 166 g of 2-chloroethanephosphonic acid dichloride and 15 g of distillation residue were obtained.

EXAMPLE 3

100 g of 2-acetoxyethanephosphonic acid dimethyl ester were heated to 230° C. while stirring. A mixture of 200 g of 2-acetoxyethanephosphonic acid dimethyl ester and 3 g of 4-(dimethylamino)-pyridine was then added dropwise at 220°–230° C. in the course of 2 hours. The reaction batch was maintained for a further 3.5 hours at 210° C. and then for 30 minutes at 200°–210° C. During the whole reaction period methyl acetate was distilled off. 117 g of methyl acetate and 6 g of dimethyl ether in a cold trap downstream of the apparatus were obtained. The resulting reaction mixture was reacted with water for 4 hours at 160° C. while stirring, during which period methanol was distilled off via a column with a silver-coated jacket. 172 g of crude vinylphosphonic acid were obtained; the water dissolved in the acid was distilled off in vacuo at 90° C. 164 g of crude anhydrous vinylphosphonic acid remained. 155 g of this crude vinylphosphonic acid were added dropwise at 140° C. in the course of 4 hours while stirring vigorously to a mixture of 129 g of 2-chloroethanephosphonic acid dichloride and 26 g of vinylphosphonic acid dichloride, during which period phosgene was passed into the reaction mixture. Thereafter phosgene was continued to be passed in for 5 hours. Excess phosgene present in the reaction batch was then flushed out by means of nitrogen at room temperature and the residue was distilled off under 0.5 mm Hg. 176 g of vinylphosphonic acid dichloride, 141 g of 2-chloroethanephosphonic acid dichloride and 20 g of a residue were obtained. The yield of vinylphosphonic acid dichloride was 72% of theory and of 2-chloroethanephosphonic acid dichloride 4.5% of theory, relative to crude vinylphosphonic acid employed.

EXAMPLE 4

50 g of 2-acetoxyethanephosphonic acid dimethyl ester and 50 g of vinylphosphonic acid were heated to 170°–185° C. while stirring. 450 g of 2-acetoxyethanephosphonic acid dimethyl ester were then added dropwise at this temperature in the course of 14.5 hours, during which period methyl acetate was distilled off simultaneously. 200 g of methyl acetate and 10 g of a low-boiling component in a cold trap downstream of the apparatus were obtained. 391 g of a reaction mixture were obtained which were then reacted with water for 9 hours at 160°–170° C. while stirring, during which period methanol was distilled off via a column with a silver-coated jacket. The resulting crude vinylphosphonic acid was freed at 90° C. in vacuo from dissolved quantities of water. 369 g of water-clear crude vinylphosphonic acid remained. 200 g of this acid were added dropwise at 140° C. in the course of 17 hours while stirring vigorously to a mixture of 166.7 g of 2-chloroethanephosphonic acid dichloride, 33.3 g of vinylphosphonic acid dichloride and 1 g of trimethylphosphine oxide, during which period phosgene was passed into the reaction mixture. Excess phosgene present in the reaction batch was then flushed out at room temperature by means of nitrogen and the residue was distilled at 0.5 mm Hg. 140 g of vinylphosphonic acid dichloride, 314.5 g of 2-chloroethanephosphonic acid dichloride and 25 g of a residue were obtained. The yield of vinylphosphonic acid dichloride was 41.5% of theory and of 2-chloroethanephosphonic acid dichloride 50.5% of theory, relative to crude vinylphosphonic acid employed.

I claim:

1. A process for the preparation of vinylphosphonic acid dichloride and 2-chloroethanephosphonic acid dichloride which comprises heating a 2-acetoxyethanephosphonic acid dialkyl ester of the general formula $$CH_3COOCH_2CH_2\overset{\overset{\displaystyle O}{\|}}{P}(OR)_2$$

ps in which R is alkyl of from 1 to 4 carbon atoms, in the presence of an acid or basic catalyst at temperature of from 150° to 270° C. with elimination of an alkyl acetate, reacting the resulting reaction mixture with water at a temperature of from 130° to 230° C. while simultaneously distilling off the alcohol formed, and reacting the crude vinylphosphonic acid thus formed with phosgene in the presence of a catalyst and also in the presence of a phosphonic acid dichloride.

2. The process as claimed in claim 1, wherein the elimination of alkyl acetate is carried out at 170° to 230° C. and the hydrolysis of the resulting reaction mixture at 140° to 175° C.

3. The process as claimed in claim 1, wherein the elimination of alkyl acetate and the phosgenation are carried out in the presence of vinylphosphonic acid.

4. The process as claimed in claim 1, wherein vinylphosphonic acid dichloride and 2-chloroethanephosphonic acid dichloride are separated by distillation.

* * * * *